United States Patent [19]

Yellin et al.

[11] Patent Number: 4,496,571
[45] Date of Patent: Jan. 29, 1985

[54] HISTAMINE H2-ANTAGONISTS

[75] Inventors: Tobias O. Yellin, Fremont, Calif.; David J. Gilman, Tytherington; Philip N. Edwards, Bramhall; Michael S. Large, Congleton; Derrick F. Jones, Tytherington; Keith Oldham, Cheadle, all of England

[73] Assignees: ICI Americas Inc., Wilmington, Del.; Imperial Chemical Industries, PLC, London, England

[21] Appl. No.: 353,422

[22] Filed: Mar. 1, 1982

[30] Foreign Application Priority Data

Feb. 27, 1981 [GB] United Kingdom ............... 8106376
May 5, 1981 [GB] United Kingdom ............... 8113664

[51] Int. Cl.³ ............... C07D 249/04; C07D 401/12; A01K 31/41
[52] U.S. Cl. ............... 514/340; 514/359; 514/256; 514/258; 514/406; 514/361; 514/364; 514/365; 514/374; 514/383; 514/396; 544/317; 544/327; 544/328; 544/329; 546/275; 546/276; 516/277; 516/278; 516/279; 548/128; 548/130; 548/132; 548/133; 548/184; 548/194; 548/232; 548/236; 548/255; 548/265; 548/266; 548/337; 548/377
[58] Field of Search ............... 546/275, 277, 276, 278, 546/279; 548/255, 128, 133, 255, 266, 236, 144, 337, 377, 130, 132, 265, 232, 184; 544/317, 327, 328, 329; 424/263, 270, 272, 273 R, 273 P, 269, 251

[56] References Cited

U.S. PATENT DOCUMENTS

| 4,165,377 | 8/1979 | Jones et al. | 424/270 |
|---|---|---|---|
| 4,165,378 | 8/1979 | Gilman et al. | 424/270 |
| 4,234,735 | 11/1980 | Jones et al. | 424/270 |
| 4,242,350 | 12/1980 | Yellin et al. | 424/270 |
| 4,242,351 | 12/1980 | Yellin et al. | 424/270 |
| 4,262,126 | 4/1981 | Gilman et al. | 424/270 |
| 4,315,009 | 2/1982 | Jones et al. | 424/270 |
| 4,332,949 | 6/1982 | Yellin et al. | 424/270 |
| 4,338,447 | 7/1982 | Yellin et al. | 424/270 |
| 4,338,448 | 7/1982 | Yellin et al. | 424/270 |
| 4,342,765 | 8/1982 | Jones et al. | 424/270 |
| 4,362,728 | 12/1982 | Yellin | 424/249 |

Primary Examiner—Robert Gerstl
Attorney, Agent, or Firm—Cushman, Darby & Cushman

[57] ABSTRACT

The invention relates to carbonyl derivatives which are histamine H-2 antagonists and which inhibit gastric acid secretion. According to the invention where is provided a guanidine derivative of the formula I:

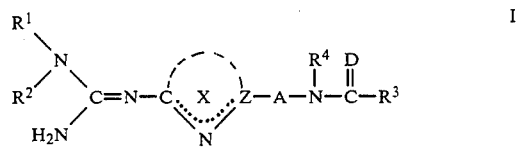

in which $R^1$ and $R^2$, same or different, are hydrogen or 1-10C alkyl, 3-8C cycloalkyl or 4-14C cycloalkylalkyl, each alkyl, cycloalkyl or cycloalkylalkyl optionally carrying one or more F, Cl or Br atoms, provided that one of $R^1$ and $R^2$ is halogen substituted, or $R^2$ is hydrogen and $R^1$ is $R^5$-E-W in which W is 2-6C alkylene optionally substituted by 1 or 2 1-4C alkyls, E is O, S, SO, $SO_2$ or $NR^6$ in which $R^6$ is H or 1-6C alkyl, $R^5$ is H or 1-6C alkyl optionally substituted by 1 or 2 1-4C alkyls, or $R^5$ and $R^6$ are joined to form a pyrrolidine, piperidine, morpholine, piperazine or N-methylpiperazine ring, or $R^2$ is H and $R^1$ is H, 1-10C alkyl, 3-8C cycloalkyl, 4-14C cycloalkylalkyl, 3-6C alkenyl, 3-6C alkynyl, 1-6C alkanoyl, 6-10C aryl, 7-11C aralkyl or 7-11C aroyl; ring X is a heterocyclic ring as defined in the specification; A is phenylene or 5-7C cycloalkylene, or a 1-8C alkylene into which is optionally inserted one or two groups; D is O or S; $R^4$ is H or 1-6C alkyl; $R^3$ is H or a variety of radicals described in the specification: and the pharmaceutically-acceptable acid-addition salts thereof. Manufacturing processes and pharmaceutical compositions are also described.

10 Claims, No Drawings

HISTAMINE H2-ANTAGONISTS

This invention relates to carbonyl derivatives which are histamine H-2 antagonists and which inhibit gastric acid secretion.

It is postulated that the physiologically-active compound histamine, which occurs naturally within the animal body, is able to combine, in the course of exerting its activity, with certain specific receptors of which there are at least two distinct and separate types. The first has been named the H-1 receptor (Ash and Schild, *Brit. J. Pharmac.*, 1966, 27, 427) and the action of histamine at this receptor is blocked (antagonised) by classical "antihistamine" drugs such as mepyramine. The second histamine receptor has been named the H-2 receptor (Black et al., *Nature*, 1972, 236, 385) and the action of histamine at this receptor is blocked by drugs such as cimetidine. It is known that one of the results of the blockade of the action of histamine at the H-2 receptor is the inhibition of the secretion of gastric acid and a compound which possesses this ability is therefore useful in the treatment of peptic ulcers and other conditions caused or exacerbated by gastric acidity.

In European Patent Publication No. 23578 and Japanese Patent Application No. J53141271 (Derwent Accession No. 05327B/03) there are described histamine H-2 antagonists and gastric secretion inhibitors respectively which are benzene and heterocyclic rings having a side chain to the end of which is attached a group —NHCOR. It has now been discovered that if an optionally-substituted guanidine radical is directly attached to certain of these heterocyclic rings there are produced potent histamine H-2 receptor antagonists.

According to the invention there is provided a guanidine derivative of the formula I:

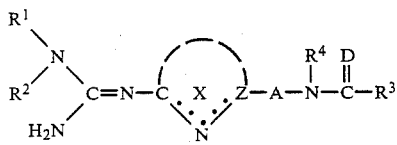

in which $R^1$ and $R^2$, which may be the same or different, are hydrogen atoms or branched or unbranched 1–10C alkyl, 3–8C cycloalkyl or 4–14C cycloalkylalkyl radicals, each alkyl, cycloalkyl or cycloalkyalkyl radical being optionally substituted by one or more halogen atoms selected from fluorine, chlorine and bromine atoms, provided that at least one of $R^1$ and $R^2$ is halogensubstituted alkyl, cycloalkyl or cycloalkylalkyl radical and provided there is no halogen substituent on the carbon atom of the alkyl, cycloalkyl or cycloalkylalkyl radical which is directly attached to the nitrogen atom, or —$R^2$ is a hydrogen atom and —$R^1$ is a radical of the formula II:

$$R^5\text{—E—W—}\qquad\qquad II$$

in which W is an unbranched 2–6C alkylene chain which is optionally substituted by one or two 1–4C alkyl radicals, E is an oxygen or sulphur atom, a sulphinyl or sulphonyl radical, or a radical of the formula $NR^6$ in which $R^6$ is a hydrogen atom or a 1–6C alkyl radical, $R^5$ is a hydrogen atom or an unbranched 1–6C alkyl radical which is optionally substituted by one or two 1–4C alkyl radicals, or $R^5$ and $R^6$ are joined to form, together with the nitrogen atom to which they are attached, a pyrrolidine, piperidine, morpholine, piperazine or N-methylpiperazine ring;

or $R^2$ is a hydrogen atom and $R^1$ is a hydrogen atom or a 1–10C alkyl, 3–8C cycloalkyl, 4–14C cycloalkylalkyl, 3–6C alkenyl, 3–6C alkynyl, 1–6C alkanoyl, 6–10C aryl, 7–11C aralkyl or 7–11C aroyl radical, the aryl, aralkyl and aroyl radicals being optionally substituted on the aryl ring by one or two substituents selected from halogen atoms and 1–6C alkyl, 1–6C alkoxy, 1–6C alkylthio, trifluoromethyl, hydroxy and amino radicals;

in ring X the dotted line is a double bond on one side of the nitrogen atom and Z is a carbon or nitrogen atom such that, when $R^1$ or $R^2$ is a halogen-substituted alkyl, cycloalkyl or cycloalkylalkyl radical or —$R^1$ is a radical of the formula II, ring X is a 5- or 6-membered heterocyclic aromatic ring which contains at least one nitrogen atom and may optionally contain one or two additional hetero atoms selected from oxygen, nitrogen and sulphur atoms, which heterocyclic ring may, where possible, carry one or two optional substituents, and when $R^2$ is a hydrogen atom and $R^1$ is a hydrogen atom or an alkyl, cycloalkyl, cycloalkylalkyl, alkenyl, alkynyl, alkanoyl, aryl, aralkyl or aroyl radical, ring X is a 1,2,3-triazole, 1,2,4-triazole, pyrazole, pyrazine, pyridine, pyrimidine or 1,3,5-triazine ring, which ring may, where possible, carry one or two optional substituents, the optional substituents on ring X being selected from fluorine, chlorine and bromine atoms and 1–6C alkyl, 1–6C alkoxy, 1–6C alkylthio, trifluoromethyl, hydroxy and amino radicals;

A is a phenylene or a 5–7C cycloalkylene radical or a 1–8C alkylene chain which is optionally substituted by one or two 1–3C alkyl radicals and into which is optionally inserted, as part of the backbone of the chain, one or two groups selected from oxygen and sulphur atoms and NH, 1–6C N-alkyl, cis and trans vinylene, ethynylene, phenylene and 5–7C cycloalklene radicals, provided that the shortest link between ring X and $NR^4$ is of at least 3 atoms, provided that when an optional insertion is made in chain A which results in the inserted group being directly attached to $NR^4$ the inserted group is other than an oxygen or sulphur atom or an NH or N-alkyl radical, and provided that no two insertions selected from oxygen and sulphur atoms and NH and N-alkyl radicals are directly attached one to the other;

D is an oxygen or sulphur atom;

$R^3$ is a hydrogen atom or a 1–6C alkyl radical which is substituted by one, two or three halogen atoms or by one or two substituents selected from hydroxy, amino, cyano, nitro, carboxy, carbamoyl, 1–6C alkoxy, 1–6C alkylthio, 1–6C alkylamino, 2–10C dialkylamino, 1–6C alkanoylamino, 6–10C aryloxy, heteroaryl, heteroaryloxy, 7–11C aroylamino, 1–6C alkanoyl, 7–11C aroyl and 2–6C alkoxycarbonyl radicals, or $R^3$ is a 2–6C alkenyl radical optionally substituted by one or two radicals selected from carboxy, carbamoyl, cyano, nitro, 2–6C alkoxycarbonyl, 7–10C aryl and heteroaryl radicals, or $R^3$ is a 1–6 C alkoxy, 2–6C alkynyl, 6–10C aryl, 7–11C arylalkyl or heteroaryl radical or a radical of the formula $COR^7$ or $CONR^7R^8$ are selected from hydrogen atoms and 1–6C alkyl and 6–10C aryl radicals, wherein when $R^3$ is or contains a heteroaryl radical that radical is a 5- or 6- membered heterocyclic aromatic ring containing 1,2 or 3 hetero atom selected from oxygen, nitrogen and sulphur atoms, which ring may be fused to a second heterocyclic ring within the same definition or to a benzene ring, and wherein when $R^3$ is or contains an aryl or heteroaryl radical, that radical may optionally be substituted by one or two substituents selected from halogen atoms and 1-6C alkyl, 1-6C alkoxy, 1-6C alkylthio, trifluoromethyl, hydroxy, amino, carbamoyl, 2-6C alkylcarbamoyl, 3-10C dialkylcarbamoyl, phenylcarbamoyl, diphenylcarbamoyl, sulphamoyl, 1-6C alkylsulphamoyl, 2-10C dialkylsulphamoyl, phenylsulphamoyl, diphenylsulphamoyl, 1-6C aminoalkyl, 2-10C alkylaminoalkyl, 3-15C dialkylaminoalkyl, 1-6C hydroxyalkyl and 2-10C alkoxyalkyl radicals and radicals of the formula III:

III in which $R^9$ and $R^{10}$ are 1-6C alkyl radicals and $R^{11}$ is a hydrogen atom or $R^9$ is a 1-6C alkyl radical and $R^{10}$ and $R^{11}$ are joined to form, together with the nitrogen and carbon atoms to which they are attached, a pyrrolidine or piperdine ring, and, when the group inserted in A is an ethynylene radical, $R^3$ may also be a 1-6C alkyl radical; $R^4$ is a hydrogen atom or a 1-6C alkyl radical;
and the pharmaceutically-acceptable acid addition salts thereof.

It is to be understood that, in the above formula I and throughout this specification, although the double bond in the guanidine residue attached to ring X has been inserted in a particular position, other tautomeric forms are possible, and this invention includes such tautomeric forms within its scope, both in terms of the compounds of the invention and in terms of the manufacturing processes. It is also to be understood that when A is or contains a cycloalkylene radical the groups attached to this radical may be in the cis or trans configuration. When A is or contains a cycloalkylene radical and/or when A is an alkylene chain substituted by one or two alkyl radicals, the compound of the formula I will, in most instances, contain at least one asymmetric centre. In such cases the compound of the formula I will therefore exist in at least two enantiomeric forms, the precise number being determined by the number of asymmetric centres. The biological activity, as hereinafter defined, of these enantiomeric forms may differ, and it is therefore to be understood that this invention encompasses the racemate of the formula I, including any possible diastereoisomeric forms, and any enantiomeric form which possesses the disclosed biological activity, it being a matter of common general knowledge to one skilled in the art how to separate diastereoisomeric forms and how to separate a racemate into its enantiomers and determine the biological activity of each.

A particular value for $R^1$ or $R^2$ when it is a nalogen-substituted alkyl radical is a 2,2,2-trifluoroethyl, 2,2,2-trichloroethyl, 2-chloro-2,2-difluoroethyl, 2,2-dichloro-2-fluoroethyl, 2-bromo-2,2-difluoroethyl, 2,2-dibromo-2-fluoroethyl, 2-fluoroethyl, 2-chloroethyl, 2,2-difluoroethyl, 2,2-dichloroethyl, 2-chloro-2-fluoroethyl, 2-bromo-2-fluoroethyl, 2,2,3,3,3-tetrafluoropropyl, 2,2,3,3,3-pentafluoropropyl, 1,1,1,3,3,3-hexafluoroisopropyl, 1,3-dichloro-1,1,3,3-tetrafluoro isopropyl, 1-chloro-1,1,3,3,3-pentafluoroisopropyl, 1,3-difluoroisopropyl or 2,2,3,3,4,4,4-heptafluorobutyl radical.

A particular value for $R^1$ or $R^2$ when it is a halogen-substituted cycloalkyl radical is a 2,2,3,3-tetrafluorocyclopropyl, 2-chloro-2,3,3-trifluorocyclopropyl, 2,2-difluorocyclopropyl, 2-chloro-3,3-difluorocyclopropyl, 2,2,3,3,4,4-hexafluorocyclobutyl or 2-chloro-2,3,3,4,4-pentafluorocyclobutyl radical.

A particular value for $R^1$ or $R^2$ when it is a halogen-substituted cycloalkylalkyl radical is a (1,2,2,3,3-pentafluorocyclopropyl)metnyl, (2-chloro-1,2,3,3-tetrafluorocyclopropyl)methyl, (1,2,2,3,3,4,4-heptafluorocyclobutyl)methyl, or (2-chloro-1,2,3,3,4,4-hexafluorocyclobutyl)methyl radical.

A particular value for $R^1$ and $R^2$ when it is an alkyl radical is a methyl, ethyl, propyl, isopropyl or butyl radical.

A particular value for $R^1$ or $R^2$ when it is a cycloalkyl radical is a cyclopropyl or cyclobutyl radical.

A particular value for $R^1$ or $R^2$ when it is a cycloalkylalkyl radical is a cyclopropylmethyl or cyclobutylmethyl radical.

A particular value for the optional substituent on W is a methyl radical.

A particular value for $R^5$ is a hydrogen atom or a methyl radical.

A particular value for $R^6$ is a hydrogen atom or a methyl radical.

A particular value for the radical of the formula II is a 2-methoxyethyl, 2-hydroxyethyl, 5-hydroxypentyl, 2-methylthioethyl or 2-dimethylaminoethyl radical.

When $R^2$ is a hydrogen atom a particular value for $R^1$ is a hydrogen atom or a methyl, ethyl, propyl, isopropyl, butyl, cyclohexyl, cyclohexylmethyl, allyl, propargyl, acetyl, phenyl, benzyl or benzoyl radical, the phenyl, benzyl and benzoyl radicals being optionally substituted on the phenyl ring by one or two substituents selected from fluorine, chlorine and bromine atoms and methyl, methoxy, methylthio, trifluoromethyl, hydroxy and amino radicals.

When $R^1$ or $R^2$ is a halogen-substituted alkyl, cycloalkyl or cycloalkylalkyl radical or a radical of the formula II, a particular value for ring X is an oxazole, thiazole, imidazole, 1,2,4-thiadiazole, 1,2,4-oxadiazole, 1,2,3-triazole, 1,2,4-triazole, pyrazole, pyrazine, pyridine, pyrimidine or 1,3,5-triazine ring.

A particular value for the optional substituent on ring X when it is an alkyl, alkoxy or alkylthio radical is a methyl, methoxy or methylthio radical.

A particular value for —A— is a phenylene, cyclopentylene, cyclohexylene, trimethylene, tetramethylene, pentamethylene, thioethylene, thiotrimethylene, thiotetramethylene, thiopentamethylene, oxyethylene, oxytrimethylene, oxytetramethylene, methylenethiomethylene, methylenethioethylene, methylenethiopropylene, methyleneoxymethylene, methyleneoxyethylene, ethyleneoxyethylene, oxy-2-methylethylene, thiopropylenethiomethylene, oxyethyleneoxymethylene, iminoethylene, iminopropylene, vinylenepropylene, oxymethylenevinylene, 1,3-phenylene, 1,3-cyclopentylene, methylene-1,4-phenylene, ethyleneoxymethylene-1,4-phenylene, oxy-1,3-phenylenemethylene or thiomethyleneethynylenemethylene radical. These values for —A— are written reading from left to right in formula I such that the first named part of the radical is attached to ring X and the last named part of the radical is attached to $NR^4$Thus, for example, when —A— is a thiomethyleneethynylenemethylene radical, the compound of the formula I contains the part structure IV:

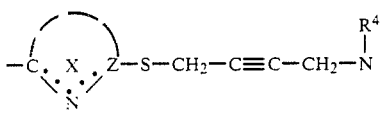

A particular value for $R^3$ is a hydrogen atom, or a methyl, ethyl, propyl or isopropyl radical each optionally substituted by one, two or three halogen atoms selected from fluorine, chlorine and bromine atoms or by one or two radicals selected from hydroxy, amino, cyano, nitro, carboxy, carbamoyl, methoxy, methylthio, methylamino, dimethylamino, acetylamino, phenoxy, heteroaryl, heteroaryloxy, benzylamino, acetyl, benzoyl and methoxycarbonyl radicals, or an allyl radical optionally substituted by one or two radicals selected from carboxy, carbamoyl, cyano, nitro, methoxycarbonyl, phenyl and heteroaryl radicals, or a methoxy, ethoxy, propargyl, phenyl, benzyl or heteroaryl radical or a radical of the formula $COR^7$ or $CONR^7R^8$ in which $R^7$ and $R^8$ are selected from hydrogen atoms and methyl and phenyl radicals, wherein when $R^3$ is or contains a heteroaryl radical that radical is furyl, thienyl, pyrrolyl, thiazolyl, oxazolyl, imidazolyl, thiadiazolyl, oxadiazolyl, triazolyl, pyrazolyl, pyridyl or pyrimidyl radical or such a radical fused to a benzene ring, and wherein when $R^3$ is or contains a phenyl or heteroaryl radical, that radical may optionally be substituted by one or two substituents selected from fluorine, chlorine and bromine atoms and methyl, methoxy, methylthio, trifluoromethyl, hydroxy, amino, carbamoyl, methylcarbamoyl, dimethylcarbamoyl, phenylcarbamoyl, diphenylcarbamoyl, sulphamoyl, methylsulphamoyl, dimethylsulphamoyl, phenylsulphamoyl, diphenylsulphamoyl, aminomethyl, methylaminomethyl, dimethylaminomethyl, hydroxymethyl and methoxymethyl radicals and radicals of the formula III given above in which $R^9$ and $R^{10}$ are methyl radicals and $R^{11}$ is a hydrogen atom, or $R^9$ is a methyl radical and $R^{10}$ and $R^{11}$ are joined to form, together with the nitrogen and carbon atoms to which they are attached, a pyrrolidine or piperidine ring.

When the group inserted in A is an ethynylene radical, a further particular value for $R^3$ is a methyl radical.

A particular value for $R^4$ is a hydrogen atom or a methyl radical.

The following are 12 preferred features of the guanidine derivative of the formula I. When any one of these features is taken, either singly or in combination, with the other general or particular features of the guanidine derivative of the formula I listed above, there are obtained preferred sub groups of compounds within the above general definition.

1. $R^2$ is a hydrogen atom and $R^1$ is a 2,2,2-trifluoroethyl, 2-chloro-2,2-difluoroethyl, 2,2,3,3-tetrafluoropropyl, 2-methoxyethyl, 2-hydroxyethyl, 5-hydroxypentyl or propyl radical.
2. $R^2$ is a hydrogen atom and $R^1$ is a 2,2,2-trifluoroethyl or 2-chloro-2,2-difluoroethyl radical.
3. Ring X carries no optional substituent.
4. Ring X is a thiazole in which A is attached at the 4-position, 1,2,3-triazole, pyridine, 1,3,5-triazine or pyrimidine in which A is attached at the 2-position, ring.
5. Ring X is a pyrimidine in which A is attached at the 2-position or 1,2,3-triazole ring.
6. A is a tetramethylene, pentamethylene, oxytrimethylene or thiotrimethylene radical.
7. Ring X is a pyrimidine ring in which A is attached at the 2-position and A is a tetramethylene, pentamethylene, oxytrimethylene or thiotrimethylene radical.
8. Ring X is a 1,2,3-triazole ring and A is a tetramethylene radical.
9. $R^4$ is a hydrogen atom.
10. D is an oxygen atom.
11. $R^3$ is a hydrogen atom or a carbamoyl, methoxymethyl, thiazol-4-yl, furan-2-yl or pyrid-3-yl radical.
12. $R^3$ is a hydrogen atom or a carbamoyl or pyrid-3-yl radical.

Specific compounds of the invention are set out in the Examples. The following is a group of preferred compounds:

N-[3-(4-[2-(2,2,2-trifluoroethyl)guanidino]pyrimid-2-ylthio)propyl]formamide (Example 10);

N-(4-[4-(2-[2,2,2-trifluoroethyl]guanidino)-1,2,3-triazol-2-yl]butyl)nicotinamide (Example 18);

N-[4-(4-[2-(2,2,2-trifluoroethyl)guanidino]pyrimid-2-yl)butyl]formamide (Example 30);

N-[5-(4-[2-(2,2,2-trifluoroethyl)guanidino]pyrimid-2-yl)pentyl]oxamide (Example 42);

N-(3-[4-(2-[2,2,2-trifluoroethyl]guanidino)pyrimid-2-yloxy]propyl)nicotinamide (Example 52);

N-(4-[4-(2-[2,2,2-trifluoroethyl]guanidino)-1,2,3-triazol-2-yl]butyl)oxamide (Example 55);

and the pharmaceutically-acceptable acid-addition salts thereof.

Among this group of compounds, the compound of Example 18 is particularly preferred.

A suitable pharmaceutically-acceptable acid-addition salt of the guanidine derivative of the formula I is, for example, a salt formed with hydrochloric, hydrobromic, phosphoric, sulphuric, acetic, citric or maleic acid.

The guanidine derivative of the invention may be manufactured by methods in which the actual chemical reactions involved are known in themselves. The following processes, $R^1$, $R^2$, $R^3$, $R^4$, A, D and ring X having the meanings stated above, unless indicated otherwise, are therefore provided as further features of the invention.

The process of the invention is characterised by:

(a) reaction of a compound of the formula V:

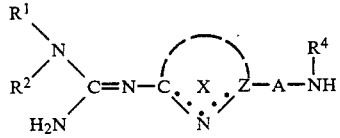

with a compound of the formula VI:

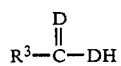

or an activated derivative thereof. The activated derivative may, for example, be the acid chloride or acid bromide, an ester, for example a 1-6C alkyl, for example methyl or ethyl, ester or an anhydride. The anhydride may be a symmetrical anhydride or a mixed anhydride. A particularly useful mixed anhydride is that formed by reaction of the acid with ethyl chloroformate. The reaction may be conducted in a diluent or solvent such as ethanol, dimethylformamide or acetonitrile. In many cases the reaction proceeds satisfactorily at ambient temperature but in certain cases, particularly those in which the activated derivative is an ester, it may be necessary to apply heat to accelerate or complete the reaction, for example by heating to the boiling point of the diluent or solvent. When an acid chloride or acid bromide is used, it is preferable to conduct the reaction in the presence of a base such as triethylamine.

(b) for those compounds in which the group inserted into A is an oxygen or sulphur atom or an NH or N-alkyl radical, reaction of a compound of the formula VII or VIII:

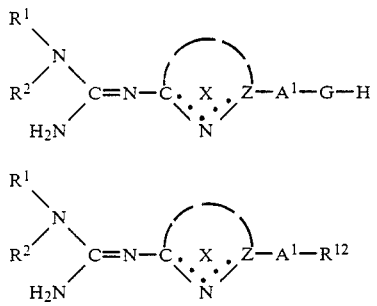

with a compound of the formula IX or X respectively:

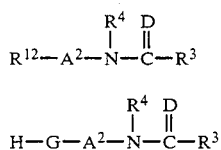

in which G is an oxygen or sulphur atom or an NH or N-alkyl radical, $R^{12}$ is a displaceable radical and $A^1$ and $A^2$ are fragments of A, including direct bonds, and are such that $A^1$—G—$A^2$ falls within the definition of A given above. $R^{12}$ is, for example, a halogen atom, for example a chlorine, bromine or iodine atom. When $R^{12}$ is directly attached to ring X $R^{12}$ may, for example, be a methylsulphinyl or methylsulphonyl radical.

(c) for those compounds in which Z is a nitrogen atom, reaction of a compound of the formula XI:

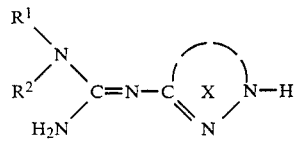

with a compound of the formula XII:

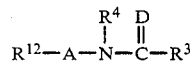

in which $R^{12}$ is a displaceable radical. $R^{12}$ is, for example, a halogen atom, for example a chlorine, bromine or iodine atom.

(d) construction of the guanidine radical attached to ring X by reaction of the appropriate thiourea, or a 1-6C S-alkyl (e.g. S-methyl) or S-benzyl derivative thereof, or a salt of such a derivative, with the appropriate amine. The guanidine radical in the compound of the formula I contains three nitrogen atoms each of which carries different substituents. The appropriate amine for use in this reaction may therefore be ammonia, an amine of the formula $R^1R^2NH$ or an amine of the formula XIII:

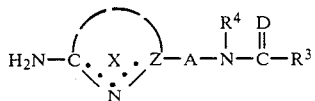

The reaction may be conducted using an excess of one of the reactants as a diluent or solvent, or an additional diluent or solvent, for example methanol or ethanol, may be added. In many cases it is advantageous to use a catalyst such as mercuric oxide, lead oxide or sodium hypochlorite. The reaction may be conducted at ambient temperature or it may be accelerated or completed by the application of heat, for example by heating to the boiling point of the diluent or solvent.

(e) construction of the guanidine radical attached to ring X by reaction of the appropriate cyanamide with the appropriate amine. Since the guanidine radical in the compound of the formula I contains only one unsubstituted nitrogen atom there are two appropriate amines, namely the amine of the formula $R^1R^2NH$ or of the formula XIII given above.

(f) for those compounds in which ring X is a thiazole ring, reaction of a compound of the formula XIV:

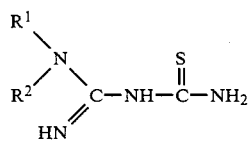

with a compound of the formula XV:

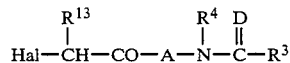

in which Hal is a chlorine or bromine atom and $R^{13}$ is a hydrogen atom or the optional substituent on the thiazole ring. The reaction may be conducted in a diluent or solvent such as acetone and may be accelerated or completed by the application of heat, for example by heating to the boiling point of the diluent or solvent.

When the process of the invention manufactures the compound of the formula I in the form of the free base and an acid-addition salt is required, the compound of the formula I in the free base form is reacted with an acid which affords a pharmaceutically-acceptable anion.

Many of the starting materials of the formula V for use in process (a) are described in Belgian Pat. No. 866155, UK Patent Application No. 2001624 and European Patent Publications Nos. 6286, 6679, 30092 and 45155, and others may be prepared by the general methods described in these publications. Thus this starting material may be obtained by separate construction of the two side chains on the appropriate ring X. Thus the left hand side chain may be constructed by reduction of a nitro group to an amino group, reaction of this amino group with an isothiocyanate of the formula $R^1R^2N$=C=S, and finally reaction of the resulting thiourea with ammonia in the presence of mercuric oxide, for example as illustrated in Examples 7 and 12. The method of construction of the right hand side chain may vary depending on the nature of ring X, the nature of the atom in ring X to which A is attached (carbon or nitrogen) and the presence or absence of inserted atoms or groups in chain A. In this construction it will generally be necessary to protect the $NR^4$—H function and to release it as a final step. When A contains no inserted group or the inserted group is a phenylene radical and Z is a carbon atom, it is preferable to construct the ring X with the right hand chain already in place. Thus when ring X is a thiazole ring a process similar to that described in process (f) may be used, for example as illustrated in Example 25. When ring X is a 1,2,3-triazole ring, it may be formed by reaction of methazonic acid with a suitable azide. When ring X is a pyrimidine ring, it may be formed by reaction of a suitably substituted imino ether or amidine with 2-chloroacrylonitrile, for example as illustrated in Example 12. When the inserted group in A is a vinylene or ethynylene radical, A may be introduced by formation of the double or triple bond by standard coupling methods. When the inserted group in A is a cycloalkylene radical, the chain A may be constructed by a conjugate addition to the corresponding cycloalk-2-enone. When the inserted group in A is an oxygen or sulphur atom or an NH or N-alkyl radical, the right hand chain may be built up by a method similar to that described in process (b), for example as illustrated in Example 7. When Z is a nitrogen atom, the right hand chain may be formed by a method similar to that described in process (c), for example as illustrated in Example 18. When $R^4$ is a hydrogen atom, a particularly useful protecting group for the nitrogen atom is the phthalimido or cyano group, for example as illustrated in Examples 7, 12, 18 and 25.

The starting material of the formula VI in process (a) in which $R^3$ carries a substituent of the formula III and the activated derivative is the acid chloride may be prepared by reaction of the corresponding acid which also carries a sulphamoyl group with thionyl chloride in the presence of a compound of the formula $R^{11}CONR^9R^{10}$, for example as illustrated in Examples 27, 49 and 50.

The starting materials of the formula VII and VIII for use in process (b), and of the formula XI for use in process (c), may be prepared by construction of the guanidine chain on a suitably substituted ring X.

The starting material of the formula XIII for use in process (d) may be prepared by the methods described above for the preparation of the starting material of the formula V for use in process (a), in which the right hand chain is constructed first, followed by process (a). During this process it may be necessary to protect the amino group attached to ring X and to remove it at the last stage.

The cyanamide, corresponding to the amine of the formula XIII, for use in process (e), may be prepared by reaction of the compound of the formula XIII with cyanogen bromide.

The starting material of the formula V for use in process (a) in which $R^2$ is a hydrogen atom, $R^1$ is a hydrogen atom or an alkyl, cycloalkyl, cycloalkylalkyl, alkenyl, alkynyl, alkanoyl, aroyl, aryl or arylalkyl radical, the last three being optionally substituted, and ring X is a 1,2,3-triazole, 1,2,4-triazole, pyrazole, pyrazine, pyridine, pyrimidine or 1,3,5-triazine ring is a particularly useful intermediate for preparing certain of the compounds of the formula I. This starting material is therefore provided as a further feature of the invention.

As noted above, the guanidine derivative of the invention is a histamine H-2 antagonist, inhibits the secretion of gastric acid in warm-blooded animals and is therefore useful in the treatment of peptic ulcers and other conditions caused or exacerbated by gastric acidity, including stress ulcers and gastrointestinal bleeding due to trauma.

The histamine H-2 antagonist activity may be demonstrated on standard tests, for example by the ability of the compound of the formula I to inhibit the histamine-induced positive chronotropic response in the spontaneously beating right atrium of the guinea pig or by its ability to inhibit the histamine-induced uptake of aminopyrine into the acid space of parietal cells.

The guinea pig atrium test is carried out as follows:

A guinea pig right atrium is suspended at 1 g. tension (isometric) in a thermostatically-controlled (30° C.) tissue bath (25 ml.) containing oxygenated (95% $O_2$, 5% $CO_2$) Krebs-Henseleit buffer (pH 7.4). The tissue is allowed to stabilise over 1 hour during which time it is washed 2–4 times. Individual contractions are recorded with a force-displacement transducer through a strain gauge coupler, and instantaneous rates are monitored with a cardiotachometer. A control response to 1 $\mu M$ histamine is obtained after which the tissue is washed 3 times and allowed to re-equilibrate to basal rate. After re-equilibration for 15 minutes, the test compound is added to the desired final concentration. Ten minutes after addition of the compound histamine (1 $\mu M$) is again added and the response to histamine in the presence of antagonist is compared to the histamine control response. The result is expressed as a percentage of the histamine control response. Thereafter the apparent dissociation constant of the H-2 antagonist is determined by standard procedures.

The aminopyrine test is carried out as follows:

Gastric mucosa from the New Zealand white rabbit is removed from the underlying muscle and washed in Buffer 1 [containing per liter NaCl; (8.007 g.), KCl (0.201 g.), $Na_2HPO_4$ (0.113 g.), $KH_2PO_4$ (0.204 g.), $CaCl_2.2H_2O$ (0.132 g.), $MgCl_2$ (0.101 g.) and glucose (1 g.), adjusted to pH 7.4 with NaOH]. The tissue is finely chopped, suspended in Buffer 1 and washed three times with Buffer 1. The tissue is then suspended in dispersion medium [collagenase (Sigma Chemical Co., Type V; 100 mg.) and bovine serum albumin (Miles Laboratories Ltd., Fraction V; 100 mg.) in Buffer 1 (100 ml.); 50 ml. per 10 g. net weight of tissue] and incubated at 30° C. and pH 7.4 (maintained by continuous monitoring) with stirring under an oxygen atmosphere. After 30 minutes the tissue is allowed to settle and the supernatant liquid is removed. Fresh dispersion medium (50 ml. per 10 g. wet weight of tissue) is added and incubation is continued with the tissue being largely dispersed into glands and whole cells afer 40–60 minutes. Any remaining large pieces of tissue are removed by filtration through nylon mesh. The mixture of glands and cells is collected by centrifugation at 200 ×g. and suspended in Buffer 1 containing 1% bovine serum albumin (Miles Laboratories Ltd., Fraction V). Finally the cells and glands are washed 3 times with Buffer 1 and suspended in Buffer 2 [containing Eagles MEM (500 ml.), Aprotinin (Sigma Chemical Co., 10 mg.) and HEPES (2-[4-(2-hydroxyethyl)piperazin-1-yl]ethanesulphonic acid; 150 mM., 20 ml.) adjusted to pH 7.4 with NaOH; 150 ml. per 10 g. net weight of tissue]. The tissue suspension is stirred under an oxygen atmosphere at 32° C. for at least 1 hour before use. The tissue suspension is incubated with the test compound and aminopyrine (10 μM) labelled with $C^{14}$ on the dimethylamino group (0.1 μCi/ml.) for 20 minutes. The uptake of the aminopyrine is then stimulated by addition of histamine and the phosphodiesterase inhibitor ICI 63197 (*Biochem.Soc.Special Publication* 1, 1973, pp 127–132) to final concentrations of $10^{-5}$M. and $5 \times 10^{-7}$M. respectively. After 18 minutes the cells/glands are separated from the incubation medium by filtration of the suspension through glass microfibre filters. The cells/glands are quickly (<10 seconds) washed three times with ice-cold Buffer 1. The $C^{14}$ aminopyrine retained by the tissue is measured on a scintillation counter and the degree of inhibition of uptake by the test compound is calculated by reference to a control sample. The concentration of test compound giving 50% inhibition is then calculated graphically from a series of tests run at different concentrations.

All the compounds exemplified in this specification were tested either on the guinea pig atrium test or on the aminopyrine test. All those tested on the guinea pig atrium test are active at or below a bath concentration of 10 μM. and the more active compounds show complete inhibition of response at this concentration. All those tested on the aminopyrine test gave a 50% inhibition of uptake of aminopyrine at or below a concentration of 3 μM.

The inhibition of the secretion of gastric acid may be demonstrated in standard tests, for example by the ability of the compound of the formula I, when dosed intravenously, intragastrically or orally, to inhibit the secretion of acidic gastric juice in, for example, rats, or dogs provided with gastric fistulae or denervated fundic pouches, and whose gastric secretion is stimulated by administration of a secretagogue, for example histamine, pentagastrin, bethanechol or food.

The test in rats is carried out as follows:

Female rats (200–230 g.) are anesthetized by intramuscular administration of urethane (1.5 g/kg.) and the trachea cannulated. A soft tube is passed down the oesophagus into the stomach and secured by a tie in the neck region. A multi-orifice plastic tube (3 mm. diameter) is passed into the antral region of the stomach, via an incision in the duodenum, and tied in place by means of a ligature around the pylorus. Saline (9 g./l. NaCl) is perfused through the stomach via the oesophageal cannula at a rate of 7 ml./minute and collected into beakers from the pyloric outlet over periods of 10 minutes Acid secretion is stimulated by subcutaneous administration of the specific H-2 agonist dimaprit in a loading dose of 10 mg./kg. followed by an infusion of 30 mg./kg./hour. Acid output is computed by titration of the 10 minute samples to an end point of pH 6.4 with 20 mM. NaOH. When secretion has reached a plateau (three consecutive readings within 5%) the test compound is administered intravenously via a cannula placed in the left external jugular vein. Secretion is then measured for a further 2 hours. A stock solution of each test compound is prepared (10 mg./ml. in DMSO) and appropriate dilution made with saline to enable injection in a dose volume of 1 ml./kg. (DMSO <2%).

The test in dogs provided with chronic fistulae is carried out as follows:

A female pure bred beagle (9–12 kg.) having a chronic gastric fistula is fasted overnight with water ad lib. During the experiment the dog is lightly restrained in a standing position. When studying the test compound by the intravenous route, the fistula is opened and, after ascertaining the absence of basal secretion over a period of 30 minutes, a continuous intravenous infusion of secretagogue (0.5 μmol./kg/hour of histamine or 2 μg./kg./hour pentagastrin) in saline (15 ml./hour) is begun. Gastric acid samples are collected every 15 minutes. The volume of each sample is measured and à 1 ml. aliquot is titrated to neutrality with 100 mM NaOH to determine acid concentration. When a plateau of secretion is reached (1–2 hours), the test compound is administered intravenously in saline and gastric acid samples are collected for a further 2–3 hours during which time the infusion of the secretagogue continues uninterrupted.

When studying the test compound by the intragastric route, the absence of basal secretion over a period of 30 minutes is ascertained and the test compound, contained in 25 ml. of 0.5% w/v hydroxypropyl methylcellulose and 0.1% w/v 'Tween' 80 in water ('Tween' is a Trade Mark) is instilled into the stomach through a fistula dosing plug. One hour later, the fistula is reopened and intravenous infusion of a secretagogue, as described above, is immediately begun. Gasteric acid samples are measured as described above and the approach of acid secretion to a plateau is compared to that of a control animal which is dosed intragastrically only with the dosing vehicle.

When studying the test compound by the oral route it is administered in a gelatin capsule with 15 ml. of water. One hour later, the fistula is opened and intravenous infusion of the secretagogue is immediately begun. Gastric acid samples are measured as above and the approcach of acid secretion to a plateau is compared to that of an undosed control animal.

The test in dogs provided with denervated fundic pouches is carried out as follows:

Male beagle dogs (14–22 kg.) are prepared with vagally denervated pouches of the fundic gland area by the method of Rudick et al. (*J. Surg. Res.* 1967, 7 383.) The animals are allowed 4–6 weeks to recover from surgery and a further period of 2–3 months prior to routine use, to allow for table training and standardization of secretory responses. The dogs are starved for 23 hours before use (water ad lib) and during experiments they are lightly restrained in cloth slings. After rinsing the pouch with warm water, histamine is infused subcutaneously at a rate of 10 μg./minute. This dose of agonist produces a submaximal (60–90% of maximum) increase in acid output in all dogs used. Pouch secretions are collected over 15 minute periods into graduated glass test-tubes and the volume measured to the nearest 0.1 ml. A 500 μl sample is diluted with 5 ml. of saline and titrated to pH 7.0 with 100 mM NaOH. Total acid output is computed from the product of acid concentration and volume of juice secreted. Compounds are administered intravenously (0.1 ml./kg.) via a cephalic vein or orally in a gelatin capsule when a secretory plateau (3 consecutive readings within 10%) has been attained. Secretion is measured for a period of 3 hours following administration of test compound.

The results obtained in the atrium and aminopyrine tests are predictive of activity in the rat and dog tests. No overt toxicity or side effects were noted during the rat or dog tests.

According to a further feature of the invention there is provided a pharmaceutical composition which comprises a guanidine derivative of the invention in association with a non-toxic pharmaceutically-acceptable diluent or carrier.

The pharmaceutical composition may, for example, be in a form suitable for oral, rectal, parenteral or topical administration, for which purposes it may be formulated by means known to the art into the form of, for example, tablets, capsules, aqueous or oily solutions or suspension, emulsions, dispersible powders, suppositories, sterile injectable aqueous or oily solutions or suspensions, gels, creams, ointments or lotions.

In addition to the guanidine derivative of the formula I, the pharmaceutical composition of the invention for oral, rectal or parenteral administration may also contain, or be co-administered with, one or more known drugs selected from antacids, for example aluminum hydroxide—magnesium hydroxide mixtures; antipepsin compounds, for example pepstatin; other histamine H-2antagonists, for example cimetidine or ranitidine; ulcer healing agents, for example carbenoxolone or bismuth salts; anti-inflammatory agents, for example ibuprofen, indomethacin, naproxen or aspirin prostaglandins, for example 16,16-dimethylprostaglandin $E_2$; classical antihistamines (histamine H-1 antagonists), for example mepyramine or diphenhydramine; anticholinergic agents, for example atropine or propantheline bromide; anxiolytic agents, for example diazepam, chlordiazepoxide or phenobarbital.

The pharmaceutical composition of the invention for topical administration may also contain, in addition to the guanidine derivative, one or more classical anti-histamines (histamine H-1 antagonists), for example mepyramine or diphenhydramine and/or one or more steroidal anti-inflammatory agents, for example fluocinolone or triamcinolone.

A topical formulation may contain 1–10% w/w of the guanidine derivative of the invention. A preferred pharmaceutical composition of the invention is one suitable for oral administration in unit dosage form, for example a tablet or capsule which contains between 5 mg. and 500 mg. of the guanidine derivative, or one suitable for intravenous, subcutaneous or intramuscular injection, for example a sterile injectable containing between 0.1% and 10% w/w of the guanidine derivative.

The pharmaceutical composition of the invention will normally be administered to man for the treatment of pepetic ulcers and other conditions caused or exacerbated by gastric acidity in the same general manner as that employed for cimetidine, due allowance being made in terms of dose levels for the potency and duration of action of the guanidine derivative of the present invention relative to cimetidine. Thus each patient will receive an oral dose of between 5 mg. and 500 mg., and preferably between 10 mg. and 100 mg., of guanidine derivative or an intravenous, subcutaneous or intramuscular dose of between 0.5 mg. and 50 mg., and preferably between 2 mg. and 20 mg., of the guanidine derivative, the composition being administered 1 to 4 times per day. The rectal dose will be approximately the same as the oral dose. The composition may be administered less frequently when it contains an amount of guanidine derivative which is a multiple of the amount which is effective when given 1–4 times per day.

The invention is illustrated, but not limited, by the following Examples. The n.m.r. spectra are quoted in δ relative to tetramethylsilane (δ=0) as internal standard (s=singlet, d=doublet, t=triplet, q=quartet, m=multiplet, br=broad). The temperatures are in degrees Centigrade. The following contractions are used:

HOAc=acetic acid
DMF=dimethyl formamide
ether=diethyl ether
DMSO=dimethylsulphoxide
MeOH=methanol
EtOH=ethanol
THF=tetrahydrofuran
EtOAc=ethyl acetate Attention is drawn to the fact that 4-nitrotriazole (Example 18) is an explosion hazard.

EXAMPLE 1

2-Furoyl chloride (145 mg.) was added to a mixture of 4-[2-(2,2,2-trifluoroethyl)guanidino]-2-(3-aminopropylthio)pyrimidine (308 mg.), EtOH (10 ml.) and triethylamine (0.5 ml.), the mixture left at room temperature for 2 hours and then evaporated to dryness. The residue was dissolved in N aqueous HCl and the solution washed with EtOAc. The aqueous phase was basified with 10 N aqueous NaOH and then extracted with EtOAc, and the extract was dried and evaporated to dryness. The residue was recrystallised from EtOAc to give N-[3-(4-[2(2,2,2-trifluoroethyl(guanidino]-pyrimidin-2-yl-thio)propyl]-2-furamide (300 mg.), m.p. 127–129°.

EXAMPLES 2–7

By a similar process to that of Example 1 using the appropriate amine and the appropriate acid chloride (except for Example 7 where acetic anhydride was used), there were obtained the compounds described in Table I.

TABLE I

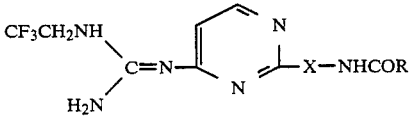

| Example | —X— | R | m.p.° | salt | Recrystallisation solvent |
|---|---|---|---|---|---|
| 2 | —S—(CH$_2$)$_3$— | 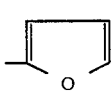 | 175–178 | hydrogen maleate | EtOH/H$_2$O |
| 3 | —(CH$_2$)$_4$— | | 150–152 | free base | EtOAc |

TABLE I-continued

Structure: CF₃CH₂NH–C(=N–)(NH₂) attached to pyrimidine ring with –X–NHCOR substituent

| Example | —X— | R | m.p.° | salt | Recrystallisation solvent |
|---|---|---|---|---|---|
| 4 | —(CH₂)₄— | –C₆H₄–SO₂NH₂ | 153–155 | free base hemihydrate | CH₃CN |
| 5 | —O—(CH₂)₃— | furan-2-yl | 169–171 | hydrogen maleate | EtOH |
| 6 | —O—(CH₂)₃— | thiazol-2-yl (N,S ring) | 168–170 | hydrogen maleate | EtOH |
| 7 | —S—CH₂C≡CCH₂— | —CH₃ | 179–181 | hydrogen maleate | EtOAc/acetone |

The 4-[2-(2,2,2-trifluoroethyl)guanidino]-2-(4-aminobut-2-ynylthio)pyrimidine used in Example 7 may be obtained as follows:

A mixture of thiocytosine (0.5 g.), N-(4-chlorobut-2-ynyl)phthalimide (1.03 g.), DMF (5 ml.) and 1,5-diazabicyclo[5,4,0] undec-5-ene (0.67 g.) was stirred for 2 hours. The solution was treated with water (20 ml.) and EtOAc (10 ml.) and the insoluble solid collected to give 4-amino-2-(4-phthalimidobut-2-ynylthio)pyrimidine (1.2 g.) m.p. 197°–202° (decomp.).

A mixture of 4-amino-2-(4-phthalimidobut-2-ynylthio)pyrimidine (1.2 g.), 2,2,2-trifluoroethylisothiocyanate (0.85 g.) and DMF (10 ml.) was stirred at 70° for 72 hours. The mixture was evaporated to dryness, and the residue stirred with N aqueous HCl and then filtered to give 4-[3-(2,2,2-trifluoroethyl)thioureido]-2-(4-phthalimidobut-2-ynylthio)pyrimidine (0.4 g.), m.p. 124–127°.

A mixture of 4-[3-(2,2,2-trifluoroethyl)thioureido]-2-(4-phthalimidobut-2-ynylthio)pyrimidine (0.37 g.), DMF (10 ml.), saturated ethanolic ammonia (1 ml.), EtOH (10 ml.) and yellow mercuric oxide (0.32 g.) was stirred at room temperature for 2 hours and then filtered and the filtrate evaporated to dryness. The residue was treated with EtOH (20 ml.) and 98% hydrazine hydrate (1 ml.) and the mixture heated under reflux for 1 hour and then evaporated to dryness. The residue was stirred with N aqueous HCl and then filtered, The filtrate was basified with 10 N aqueous NaOH and the mixture extracted four times with ether. The combined extracts were dried and evaporated to dryness to give 4-[2-(2,2,2-trifluoroethyl)guanidino]-2-(4-aminobut-2 -ynylthio)pyrimidine (0.17 g.) characterised as the bis hydrogen maleate, m.p. 153°–155° (decomp.)

EXAMPLE 8

By a similar process to that of Example 1 using 6-[2-(2,2,2-trifluoroethyl)guanidino]-2-[(2-aminoethyl)-thiomethyl]pyridine as starting material, there was obtained N-[2-(6-[2-(2,2,2-trifluoroethyl)guanidino]-pyrid-2-yl-methylthio)ethyl]-2-furamide hydrogen maleate, m.p. 134°–136°.

EXAMPLE 9

A mixture of 4-[2-(2,2,2-trifluoroethyl)guanidino]-2-(3-aminopropylthio)pyrimidine (0.15 g.), EtOH (5 ml.) and ethyl oxamate (0.06 g.) was stirred at room temperature for 18 hours. More ethyl oxamate (20 mg.) was added and the solution was heated under reflux for 2 hours and then evaporated to dryness. The residue was dissolved in N HCl and the solution washed with EtOAc, and then basified with 10 N aqueous NaOH. The mixture was extracted with EtOAc, and the extract dried and evaporated to dryness. A solution of the residue in acetone was added to a solution of maleic acid in acetone and the precipitated salt collected and recrystallised from EtOH to give N-[3-(4-[2-(2,2,2-trifluoroethyl)guanidino]-pyrimid-2-ylthio)propyl]oxamide hydrogen maleate, m.p. 200–201°.

EXAMPLE 10

A mixture of 4-[2-(2,2,2-trifluoroethyl)guanidino]-2-(3-aminopropylthio)pyrimidine (0.3 g.), ethyl formate (5 ml) and EtOH (2 ml.) was heated under reflux for 48 hours, then evaporated to dryness. The residue was dissolved in N aqueous HCl and the solution washed with EtOAc. The aqueous phase as basified with 10 N aqueous NaOH, extracted with EtOAc and the extract dried and evaporated to dryness. The residue was recrystallised from EtOAc to give N-[3-(4-[2-(2,2,2-trifluoroethyl)guanidino]pyrimid-2-ylthio)propyl]-formamide (0.2 g.), m.p. 165°–166°.

EXAMPLE 11

By a similar process to that of Example 9, using ethyl 2-methoxyacetate as starting material, there was obtained N-[3-(4-[2(2,2,2-trifluoroethyl)-guanidino]pyrimid-2-ylthio)propyl]-2-methoxyacetamide hydrogen maleate, m.p. 177°–178°.

EXAMPLE 12

Nicotinoyl chloride hydrochloride (0.2 g.) was added at 0° to a stirred solution of 4-(2-propyl-guanidino)-2-(5-aminopentyl)pyrimidine (0.2 g.) in EtOH (5 ml.) and triethylamine (2 ml.). The mixture was stirred at room temperature for 16 hours and evaporated to dryness. The residue was partitioned between 2 N aqueous HCl and EtOAc and the aqueous phase was then basified with 10 N aqueous NaOH and extracted with EtOAc. The extract was dried (MgSO$_4$) and evaporated to dryness. The residual gum was purified twice by preparative thin layer chromatography on Merck 60 F-254 plates using EtOAc/MeOH/aqueous ammonia (s.g. 0.88) 6:1:1 v/v/v as developing solvent. The appropriate zone of the chromatogram was extracted with MeOH/aqueous ammonia (s.g. 0.88) 10:1 v/v and the solvent was evaporated. The residual gum was dissolved in EtOAc, filtered and treated with an excess of a saturated solution of maleic acid in EtOAc. The precipitated gum was washed with EtOAc to give N-[5-(4-[2-propylguanidino]-pyrimid-2-yl)pentyl]nicotinamide (0.015 g.) as a straw coloured gum. The n.m.r. spectrum in d$_4$ MeOH using tetramethylsilane as standard included the following resonances (δ):1.0 (3H, triplet), 1.7 (8H, multiplet), 2.9 (2H, triplet), 3.6 (2H, triplet), 6.8 (1H, doublet), 7.6 (1H, multiplet), 8.3 (2H, multiplet) and 8.8 (2H, complex).

The 4-[2-propylguanidino]-2-(5-aminopentyl)-pyrimidine used as starting material may be obtained as follows:

Into a stirred solution of 6-phthalimidohexanenitrile (30 g.) in dry THF (150 ml.) and EtOH (9 ml.) at 0° was bubbled HCl gas for one hour. The mixture was allowed to stand at 5° for 24 hours then evaporated. The residual oil was dissolved in MeOH (100 ml.) and treated with ammonium chloride (8 g.). The slurry was stirred whilst a solution of sodium (2.85 g.) in MeOH (100 ml.) was added. The mixture was stirred for 16 hours, evapoated to dryness and the residue was then dissolved in EtOH (200 ml.), filtered and evaporated to dryness. The residue was triturated with EtOAc to give 6-phthalimidohexanamidine hydrochloride (19.4 g.), m.p. 149°-151°.

A mixture of 6-phthalimidohexanamidine hydrochloride (71.1 g.), triethylamine (170 ml.) and 2-chloroacrylonitrile (57.4 ml.) in EtOH (500 ml.) was heated under reflux for 2 hours. The solvent was evaporated and the residue was partitioned between EtOAc and 2 N aqueous HCl. The aqueous layer was basified with 10 N aqueous NaOH and the product was extracted with EtOAc, dried (MgSO$_4$) and evaporated to dryness. The residual gum was dissolved in EtOAc and treated with excess of a solution of maleic acid in EtOAc. The precipitated solid was dissolved in water, basified with 10 N aqueous sodium hydroxide, extracted with EtOAc, the extract dried (MgSO$_4$) and evaporated. The residual solid was triturated with acetonitrile to give 4-amino-2-(5-phthalimidopentyl)pyrimidine as a brown solid (37.9 g.), m.p. 101°-104°.

A mixture of 4-amino-2-(5-phthalimidopentyl)pyrimidine (2 g.) and propylisothiocyanate (1 g.) in pyridine (5 ml.) was heated under reflux for 16 hours then evaporated to dryness. The residual solid was triturated with acetonitrile to give 4-(3-propylthioureido)-2-(5-phthalimidopentyl)pyrimidine (1.7 g.), m.p. 146°-149°.

A mixture of 4-(3-propylthioureido)-2-(5-phthalimidopentyl)pyrimidine (1.7 g.), DMF (25 ml.) saturated ethanolic ammonia (10 ml.) and yellow mercuric oxide (1.1 g.) was stirred at room temperature for 2 hours. The mixture was evaporated to dryness and the residue was redissolved in ethanol, filtered and the filtrate evaporated to dryness. A solution of this residue in EtOH (20 ml.) was treated with hydrazine (5 ml.) and stirred at room temperature for 16 hours. The mixture was evaporated to dryness and the residue was dissolved in water, acidified with 2 N aqueous HCl and filtered. The filtrate was basified with 10 N aqueous NaOH and the mixture was extracted twice with EtOAc. The extract was dried (MgSO$_4$) and evaporated to give 4-[2-propylguanidino]-2-(5-aminopentyl)-pyrimidine as a gum (0.4 g.) which was used without further purification.

EXAMPLE 13

Ethyl chloroformate (0.14 ml.) was added to a stirred mixture of 3-(imidazol-4-yl)propionic acid (0.3 g.) and triethylamine (2 ml.) in DMF (5 ml.) at 0° and the mixture stirred at 0° for 0.5 hours. 4-[2-(2,2,2-Trifluoroethyl)guanidino]-2-(5-aminopentyl)pyrimidine (0.3 g.) in DMF (2 ml.) was added to the mixture and stirring was continued at room temperature for 16 hours. The mixture was evaporated and the residue partitioned between EtOAc and 2 N aqueous HCl. The acid layer was basified with 11 N aqueous NaOH, extracted with EtOAc, dried (MgSO$_4$) and evaporated to dryness. The residual gum was dissolved in EtOAc and treated with excess of a solution of maleic acid in EtOAc. The resulting solid was filtered and recrystallised from EtOH-/EtOAc to give N-[5-(4-[2-(2,2,2-trifluoroethyl)-guanidino]pyrimid-2-yl)pentyl]-3-(imidazol-4-yl)propionamide bis maleate hemihydrate (containing 0.5 EtOH of crystallisation) (0.2 g.), m.p. 136°-141° (decomp.).

The intermediate 4-[2-(2,2,2-trifluoroethyl)-guanidino]-2-[5-aminopentyl]pyrimidine used above may be prepared in an analogous manner to that described for the preparation of 4-(2-propylguanidino)-2-(5-aminopentyl)pyrimidine in Example 12, parts 5 and 6, using 2,2,2-trifluoroethylisothiocyanate in place of propylisothiocyanate.

EXAMPLE 14

Triethylamine (3 ml.) was added to a mixture of ethyl chloroformate (0.06 ml.) and 4-[2-(2,2,2-trifluoroethyl)-guanidino]-2-(5-aminopentyl)pyrimidine (0.2 g.) in DMF (3 ml.) at 0°. The mixture was stirred at room temperature for 1 hour and then evaporated to dryness. The residual gum was partitioned between EtOAc and 2 N aqueous HCl and the acid layer was then basified with 11 N aqueous sodium hydroxide and extracted with EtOAc. The organic layer was dried (MgSO$_4$) and evaporated. The residual gum was redissolved in EtOAc and treated with an excess of a solution of maleic acid in EtOAc. The resulting solid was filtered to give ethyl N-[5-(4-[2-(2,2,2-trifluoroethyl)guanidino]-pyrimid-2-yl)pentyl]carbamate hydrogen maleate (0.11 g.), m.p. 150°-154°.

EXAMPLES 15-16

Ethyl chloroformate (0.07 ml.) was added to a mixture of imidazole-4-carboxylic acid (0.08 g.) and triethylamine (1 min.) in DMF (5 ml.) at -5°. The mixture was stirred at room temperature for 0.5 hours and then treated with a solution of 4-[2-(2,2,2-trifluoroethyl)-guanidino]-2-(4-aminobutyl)pyrimidine (0.2 g.) in DMF (2 ml.). The mixture was stirred at room temperature for 4 hours, then evaporated to dryness. The residual gum was partitioned between EtOAc and 2 N aqueous HCl and the acid layer was then basified with 11 N aqueous sodium hydroxide and extracted with EtOAc. The organic layer was dried (MgSO$_4$) and evaporated to dryness. The residual gum was purified by preparative thin layer chromatography on Merck 60 F-254 plates using EtOAc/MeOH/aqueous ammonia (s.g. 0.88) 6:1:1 v/v/v as developing solvent. Two products were obtained by extracting appropriate bands of the chromatogram using MeOH/aqueous ammonia (s.g. 0.88) 10:1 v/v and evaporating to dryness. Both residual gums were dissolved in EtOAc and treated with excess of a solution of maleic acid in EtOAc. The resulting solids were filtered to give the separate products.

The more polar band gave N-[4-(4-[2-(2,2,2-trifluoroethyl)guanidino]pyrimid-2-yl)butyl]imidazol-4-ylcarboxamide bis maleate (0.02 g.), m.p. 155°–159° (decomp.).

The less polar band gave ethyl N-[4-(4-[2-(2,2,2-trifluoroethyl)guanidino]pyrimid-2-yl)butyl]-carbamate hydrogen maleate monohydrate (0.06 g.), m.p. 152°–156°.

EXAMPLE 17

A stirred mixture of unpurified 2-mercapto-4-(2-[2,2,2-trifluoroethyl]guanidino)-1,3,5-triazine (0.126 g.), N-(3-bromopropyl)-2-furamide (0.126 g.), aqueous NaOH (10% w/v; 0.2 ml.), and water (1 ml) was kept at room temperature overnight. The mixture was filtered to give a white solid which was washed with water, then with EtOH, and then with petroleum ether (b.p. 40°–60°). The product was purified by preparative t.l.c. using CH$_2$Cl$_2$/MeOH/aqueous ammonia (s.g. 0.880) 9:1:0.1 v/v/v as eluant to give 0.03 g. of N-(3-[4-(2-[2,2,2-trifluoroethyl]guanidino)-1,3,5-triazin-2-yl-thio]-propyl)-2-furamide, m.p. about160°. C$_{14}$H$_{16}$F$_3$N$_7$O$_2$S requires C 41.7, H 4.0, N 24.0; found C 41.3; H 4.0, N 24.0%.

The starting materials may be prepared as follows:

A stirred mixture of 3-bromopropylamine hydrobromide (2.2 g.) and CH$_2$Cl$_2$ (20 ml.) was treated at room temperature with triethylamine (2.8 ml.). The mixture was stirred at room temperature for 10 minutes and then treated dropwise with 2-furoyl chloride (1.0 ml.). The mixture was stirred overnight at room temperature and then partitioned between water and CH$_2$Cl$_2$. The organic phase was separated, dried (MgSO$_4$), and evaporated. The residual oil was purified by chromatography on silica gel using EtOAc/petroleum ether (b.p. 60°–80°) 1:1 v/v as eluant to give 1.7 g. of N-(3-bromopropy)-2-furamide.

A stirred mixture of 2-mercapto-4-amino-1,3,5-triazine (2.56 g.), 4-methoxybenzylbromide (4.4 g.), 1,8-diazabicyclo[5,4,0]undec-7-ene (3.3 ml.) and EtOH (30 ml.) was kept at room temperature for 4 hours. The mixture was filtered. The retained solid was triturated with aqueous NaOH (10% w/v), refiltered, washed with water, and recrystallised from dioxan to give 3.3 g. of 4-amino-2-(4-methoxybenzyl)thio-1,3,5-triazine, m.p. 203°–204°.

A stirred mixture of 4-amino-2-(4-methoxybenzyl)thio-1,3,5-triazine (2.48 g.) and THF (100 ml.) was treated at 15° under an atmosphere of argon with methyl magnesium bromide (3M; 4.0 ml.). The reaction temperature rose to 20°. The mixture was kept at 20° for 15 minutes and then treated with 2,2,2-trifluoroethyliso- thiocyanate (1.7 g.). The mixture was stirred at room temperature overnight, poured into water (100 ml.) and the mixture evaporated. The residue was partitioned between water and EtOAc to give a mixture which was filtered. The filtrate was evaporated and the residue was recrystallised from MeOH to give 1.85 g. of 2-(4-methoxybenzyl)thio-4-[3-(2,2,2-trifluoroethyl)thioureido]-1,3,5-triazine, m.p. 178°–180°.

A stirred mixture of 2-(4-methoxybenzyl)thio-4-[3-(2,2,2-trifluoroethyl)thioureido]-1,3,5-triazine (1.6 g.), DMF (20 ml.), and ammonical EtOH (6M; 20 ml.) was treated at room temperature with mercuric oxide (1.3 g.). The mixture was kept at room temperature for 4 days. The mixture was filtered and evaporated to give 1.9 g. of 2-(4-methoxybenzyl)thio-4-[2-(2,2,2-trifluoroethyl)guanidino]-1,3,5-triazine. R$_f$ 0.5 (silica gel/EtOAc).

A stirred mixture of unpurified 2-(4-methoxybenzyl)thio-4-[2-(2,2,2-trifluoroethyl)guanidino]-1,3,5-triazine (1.0 g.) and trifluoroacetic acid (5 ml.) was kept at room temperature for 4 days. The mixture was evaporated to dryness. The residue was partitioned between dilute aqueous NaOH and ether. The aqueous phase was separated, acidified to pH 4 and filtered to give 0.245 g. of 2-mercapto-4-(2-[2,2,2-trifluoroethyl]-guanidino)-1,3,5-triazine which was used without further purification.

EXAMPLE 18

A stirred mixture of unpurified 4-(4-[2-(2,2,2-trifluoroethyl)guanidino]-1,2,3-triazol-2-yl)butylamine (0.5 g.), triethylamine (0.5 ml.), and acetonitrile (10 ml.) was treated dropwise at −10° with nicotinoyl chloride hydrochloride (0.5 g.). The mixture was allowed to warm to room temperature and kept for 4 hours. The mixture was evaporated and the residue partitioned between EtOAc and water. The organic layer was separated and extracted with dilute hydrochloric acid, The acid extract was neutralised with NaOH and extracted with EtOAc. The organic extract was dried (MgSO$_4$) and evaporated to give an oil. A solution of this oil in a small volume of EtOAc was treated with a solution of maleic acid (0.21 g.) in a small volume of acetone and then with ether to give an oil which crystallised on standing at room temperature overnight. The crystals were isolated by filtration, washed with ether and then with EtOAc, and recrystallised from isopropanol/ether to give a first crop of 0.17 g. and a second crop of 0.1 g. of N-(4-[4-(2-[2,2,2-trifluoroethyl]guanidino)-1,2,3-triazol-2-yl]butyl)nicotinamide maleate, m.p. 160°–162°.

The starting material may be prepared as follows:

A stirred solution of 4-nitro-1,2,3-triazole (5.7 g.) in dry DMF (30 ml.) was treated at room temperature with a dispersion of sodium hydride (1,2 g.) in mineral oil (1.2 g.). The mixture was stirred for 30 minutes and then treated with 4-bromobutyronitrile (7.5 g.). The mixture was stirred overnight at room temperature and then poured into water. The product was extracted into EtOAc, washed with brine, dried (MgSO$_4$), and evaporated to give an oil. This oil was purified by column chromatography on silica gel using CH$_2$Cl$_2$/EtOAc 19:1 v/v as eluant to give 5.4 g. of 4-(4-nitro-1,2,3triazol-2-yl)butyronitrile as an oil.

A suspension of palladium on charcoal (5% w/w; 0.5 g.) in a solution of 4-(4-nitro-1,2,3-triazol-2-yl)-butyronitrile (1.0 g.) in HOAc (15 ml.) was stirred under one atmosphere of hydrogen until 500 ml. of hydrogen had been absorbed. The mixture was filtered and evaporated to give 0.8 g. of 4-(4-amino-1,2,3-triazol-2-yl)butyronitrile.

A solution of 4-(4-amino-1,2,3-triazol-2-yl)butyronitrile (0.4 g.) and 2,2,2-trifluoroethylisothiocyanate (0.5 g.) in acetonitrile (5 ml.) was stirred at room temperature for 2 hours. The mixture was filtered. The retained solid was washed with acetonitrile to give 0.28 g. of 4-(4-[3-(2,2,2-trifluoroethyl)trioureido]-1,2,3-triazol-2-yl)butyronitrile, m.p. 160°–162°.

A stirred solution of 4-(4-[3-(2,2,2-trifluoroethyl)thioureido]-1,2,3-triazol-2yl)butyronitrile (2.0 g.) in ammoniacal EtOH (6M; 20 ml.) was treated at room temperature with mercuric oxide (2.5 g.). The mixture was stirred at room temperature overnight. The mixture was filtered and evaporated to give 2.0 g. of unpurified 4-(4-[2-(2,2,2-trifluoroethyl)guanidino]-1,2,3-triazol-2-yl)butyronitrile as an oil. A small sample was converted into its maleate salt, m.p. 136°–138°.

A suspension of Raney nickel (about 3 g.) in a solution of unpurified 4-(4-[2-(2,2,2-trifluoroethyl)guanidino]-1,2,3-triazol-2-yl)butyronitrile (1.8 g.) in ammoniacal EtOH (6M; 50 ml.) was stirred under one atmosphere of hydrogen until 230 ml. of hydrogen had been absorbed. The mixture was filtered and evaporated to give 1.3 g. of 4-(4-[2-trifluoroethyl)guanidino]-1,2,3-triazol-2-yl)butylamine which was used without further purification.

EXAMPLES 19–56

Amides of the formula:

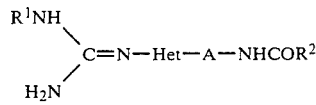

were prepared from amines of the formula:

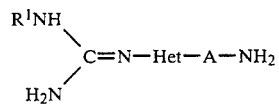

by the process described in Example 1 (acid chloride, AC), Example 13 (mixed anhydride, MA) or Example 10 (ester, E), as indicated in the last column of the Table (except for the products in Examples 34, 41, 42, 45, 47, 53 and 55 which were prepared by the methods indicated in the Notes at the foot of the Table).

| Example | $R^1$ | —Het— | —A— | —$R^2$ | Process |
|---|---|---|---|---|---|
| 19 | $CF_3CH_2$ | thiazole | $-(CH_2)_4-$ | phenyl-$SO_2NH_2$ | AC |
| 20 | $CF_3CH_2$ | thiazole | $-(CH_2)_4-$ | furan | AC |
| 21 | $HOCH_2CH_2$ | thiazole | $-(CH_2)_4-$ | furan | AC |
| 22 | $CH_3OCH_2CH_2$ | thiazole | $-(CH_2)_4-$ | phenyl-$SO_2NH_2$ | AC |
| 23 | $CF_3CH_2$ | thiazole | $-(CH_2)_4-$ | pyridine | AC |
| 24 | $CH_3OCH_2CH_2$ | thiazole | $-(CH_2)_5-$ | phenyl-$SO_2NH_2$ | AC |
| 25 | $HO(CH_2)_5$ | thiazole | $-(CH_2)_4-$ | phenyl-$SO_2NH_2$ | AC |
| 26 | $CH_3OCH_2CH_2$ | thiazole | $-(CH_2)_5-$ | furan | AC |

| 27 | CF$_3$CH$_2$ |  | —(CH$_2$)$_4$— |  | AC |
| 28 | CF$_3$CH$_2$ |  | —(CH$_2$)$_5$— | —CH=CH—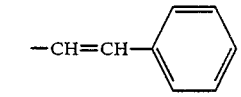 | AC |
| 29 | CF$_3$CH$_2$ | 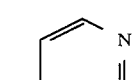 | —(CH$_2$)$_5$— | 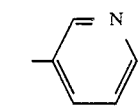 | AC |
| 30 | CF$_3$CH$_2$ | 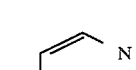 | —(CH$_2$)$_4$— | —H | E |
| 31 | CF$_3$CH$_2$ | 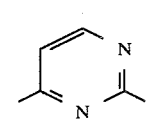 | —(CH$_2$)$_4$— | —CH$_2$O—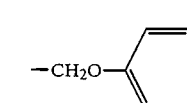 | MA |
| 32 | CF$_3$CH$_2$ |  | —(CH$_2$)$_5$— | 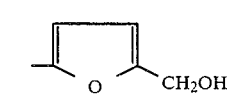 | MA |
| 33 | CF$_3$CH$_2$ | 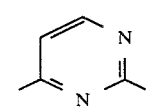 | —(CH$_2$)$_4$— | —CH$_2$CH$_2$—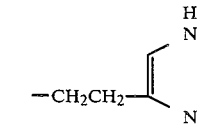 | MA |
| 34 | CF$_3$CH$_2$ | 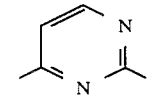 | —(CH$_2$)$_5$— | —CF$_3$ | — |
| 35 | CF$_3$CH$_2$ |  | —(CH$_2$)$_4$— | —CH$_2$CH$_2$—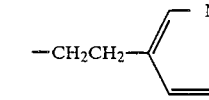 | MA |
| 36 | CF$_3$CH$_2$ | 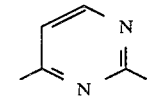 | —(CH$_2$)$_5$— | 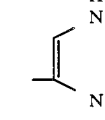 | MA |
| 37 | CF$_3$CH$_2$ |  | —(CH$_2$)$_4$— | 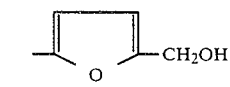 | MA |
| 38 | CF$_3$CH$_2$ |  | —(CH$_2$)$_4$— | —CH=CH—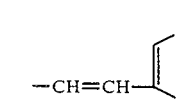 | MA |

-continued
| | | | | | |
|---|---|---|---|---|---|
| 39 | CF₃CH₂ | 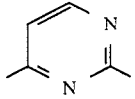 | —(CH₂)₄— | —CH=CH—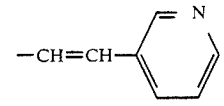 | MA |
| 40 | CF₃CH₂ | 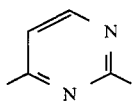 | —(CH₂)₄— | —COOC₂H₅ | AC |
| 41 | CF₃CH₂ | 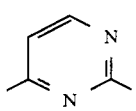 | —(CH₂)₄— | —CONH₂ | — |
| 42 | CF₃CH₂ | 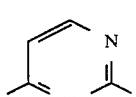 | —(CH₂)₅— | —CONH₂ | — |
| 43 | CF₃CH₂ | 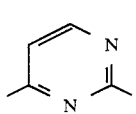 | —(CH₂)₅— | —(CH₂)₃—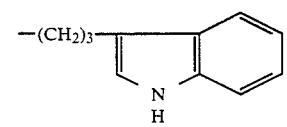 | MA |
| 44 | CF₃CH₂ | 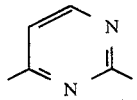 | —(CH₂)₅— | 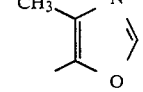 | MA |
| 45 | CClF₂CH₂— | 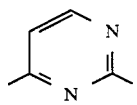 | —(CH₂)₅— | —CF₃ | — |
| 46 | CClF₂CH₂— | 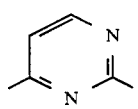 | —(CH₂)₅— | 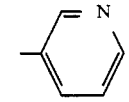 | AC |
| 47 | CClF₂CH₂— | 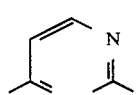 | —(CH₂)₅— | —CONH₂ | — |
| 48 | CF₃CH₂ | 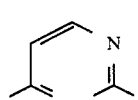 | —(CH₂)₅— | 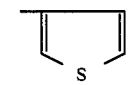 | MA |
| 49 | CF₃CH₂ | 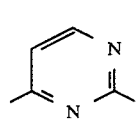 | —S(CH₂)₃— | 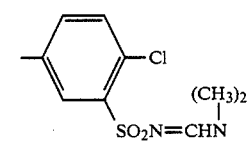 | AC |
| 50 | CF₃CH₂ | 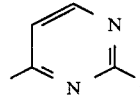 | —S(CH₂)₃— | 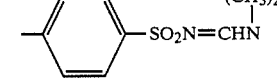 | AC |
| 51 | CF₃CH₂ | 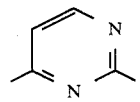 | —S(CH₂)₃— | 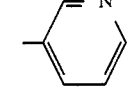 | AC |

| | | Het | A | R² | Salt |
|---|---|---|---|---|---|
| 52 | CF₃CH₂ | pyrimidine (as shown) | —O(CH₂)₃— | pyridyl | AC |
| 53 | CF₃CH₂ | pyrimidine | —O(CH₂)₃— | —CONH₂ | — |
| 54 | CF₃CH₂ | pyrimidine | —O(CH₂)₃— | H | E |
| 55 | CF₃CH₂ | pyrazole | —(CH₂)₄— | —CONH₂ | — |
| 56 | CF₃CH₂ | pyrazole | —(CH₂)₄— | —CH₂NHCOCH₃ | MA |

Notes

In the above Table the group $R^1NHC(NH_2)=N-$ is attached to the left-hand bond of the heterocyclic ring (—Het—) and the group —A— is attached to the right-hand bond of the heterocyclic ring (—Het—). Similarly, the left-hand bond of —A— is attached to the heterocyclic ring (—Het—) and the right hand bond of —A— is attached to NHCOR².
Thus the product in Example 53 has the formula:

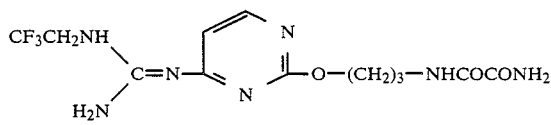

Example 19: n.m.r. in d₆DMSO: 1.6 (m, 4H); 2.5 (m, under solvent); 3.1 (q, under solvent); 4.0 (q, 2H9; 6.3 (s, 1H); 7.9 (q, 4H). (Yield 20%).
Example 20: n.m.r. in d₆DMSO: -1.6 (m, 4H); 2.5 (m, under solvent ); 3.2 (q, under solvent ); 4.0 (m, 2H); 6.35 (s, 1H); 6.55 (q, 1H,); 7.0 (d, 1H); 7.75 (s, 1H). (Yield 70%).
Example 21: fumarate, m.p. 180–182°(yield 20%).
Example 22: m.p. 155–157° (yield 30%).
Example 23: m.p. 166–169°(yield 20%).
Example 24: maleate, m.p. 168–170°(yield 35%).
Example 25: oxalate, calculated C, 47.8; H, 5.9; N, 15.9: found C, 47.4; H, 6.2: N, 15.9%. The intermediate 2-[2-(5-hydroxypentyl)guanidinol]-4-(4-aminobutyl)-thiazole may be prepared by a procedure similar to that described for 2-[2-(2-hydroxyethyl)guanidinol]-4-(4-aminobutyl)thiazole in Example 4 of European Patent Publication No. 45155, using 5-hydroxypentylamine in place of ethanolamine.
Example 26: m.p. 169–172° (yield 75%).
Example 27: maleate, m.p. 107–110° (yield 33%). The required acid chlorine was prepared by heating 4-chloro-3-sulphamoylbenzoic acid in thionyl chloride and N—methylpyrrolid-2-one under reflux.
Example 28: maleate, m.p. 152° (yield 33%). The 4-[2-(2,2,2-trifluoroethyl)guanidinol]-2-[5-aminopenyl]-pyrimidine used as starting material may be prepared by the procedure described in European Patent Publication No. 30092, Example 4, using 6-phthalimidohexanenitrile in place of 5-phthalimidopentanentrile.
Example 29: 2 maleate, m.p. 84° (yield 18%).
Example 30: maleate, m.p. 166–169° (yield 21%).
Example 31: 1.75 maleate, m.p. 111–114° (yield 9%).

-continued

Example 32: maleate, m.p. 143–148° (yield 15%).
Example 33: 1.5 maleate, m.p. 131° (yield 31%).
Example 34: maleate, 0.5 EtOH, m.p. 149–154° (yield 45%). Prepared using trifluoroacetic anhydride.
Example 35: 1.75 maleate 2.5 H$_2$O, m.p. 76–79° (yield 33%).
Example 36: 2 maleate, m.p. 84–88° (yield 8%).
Example 37: 0.75 maleate, 1 H$_2$O, m.p. 105–110° (yield 20%).
Example 38: 2.5 maleate, 1 H$_2$O, m.p. 124° (yield 14%).
Example 39: 2.25 maleate 1 H$_2$O, m.p. 145° (yield 36%).
Example 40: maleate 0.5 H$_2$O, m.p. 131–135° (yield 40%).
Example 41: m.p. 206–209° (yield 61%). Prepared by the process of Example 9.
Example 42: 1.25 maleate, m.p. 180–183° (yield 37%). Prepared by the process of Example 9.
Example 43: 1.5 maleate, m.p. 133–137° (yield 28%).
Example 44: maleate, m.p. 129–132° (yield 2%).
Example 45: maleate, 165–168° (yield 50%). Prepared from (CF$_3$CO)$_2$O and 4-[2-(2-chloro-2,2-difluoroethyl]duanidinol]-2-[5-aminopentyl]pyrimidine which may itself be prepared by a procedure similar to that described in Example 4 of European Patent Publication No. 30093, using 2-chloro-2,2-difluoroethylisothiocyanate in place of 2,2,2-trifluoroethylisothiocyanate and 6-phthalimidohexaneitrile in place of 5-phthalimido-pentanenitrile.
Example 46: 2 maleate, 0.5 H$_2$O, m.p. 116–120° (yield 77%).
Example 47: maleate, m.p. 202° (yield 12%). Prepared by the process of Example 9.
Example 48: maleate, m.p. 157–162° (yield 38%).
Example 49: maleate, m.p. 154–157° (yield 21%). The required acid chloride was prepared by heating 4-chloro-3-sulphamoylbenzoic acid and thionyl chloride in DMF under reflux.
Example 50: maleate, m.p. 181–183° (yield 68%). The required acid chloride was prepared by heating 4-sulphamoylbenzoic acid and thionyl chloride in DMF under reflux.
Example 51: 1.25 maleate, m.p. 174–176° (yield 43%).
Example 52: 1.5 maleate, m.p. 143–145° (yield 32%).
Example 53: m.p. 208–209° (yield 62%). Prepared by the process of Example 9.
Example 54: maleate, m.p. 159–161° (yield 40%).
Example 55: m.p. 144–146° (yield 65%). Prepared by the process of Example 9.
Example 56: maleate, 158–159° (yield 21%).

EXAMPLE 57

A tablet containing 50 mg. of N-(4-[4-(2-[2,2,2-trifluoroethyl]guanidino)-1,2,3-triazol-2-yl]butyl)nicotinamide may be prepared using ingredients in the following proportions:

| | | mg./tablet |
|---|---|---|
| (a) | Tablet Core. | |
| | Active agent | 50 |
| | Lactose | 218.5 |
| | Calcium carboxymethylcellulose | 22.5 |
| | Polyvinylpyrrolidone | 6.0 |
| | Magnesium stearate | 3.0 |
| (b) | Tablet Coat | |
| | Hydroxypropylmethylcellulose | 4.5 |
| | Polyethylene glycol | 0.9 |
| | Titanium dioxide | 1.35 |

The active agent, lactose and calcium carboxymethylcellulose are mixed. An aqueous solution of polyvinylpyrrolidone is added, and the mass is then mixed until it is suitable for granulation. The mass is then granulated and dried. The magnesium stearate is blended with the dried granules and the resulting mixture is compressed into tablets. The tablets are film-coated using an aqueous or solvent suspension of hydroxypropylmethylcellulose, polyethylene glycol and titanium dioxide.

We claim
1. A guanidine derivative of the formula I:

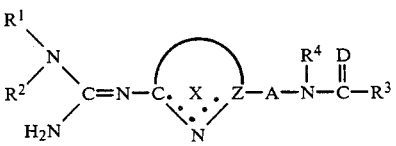

in which
R$^1$ and R$^2$, which may be the same or different, are hydrogen atoms or branched or unbranched 1–10C alkyl, 3–8C cycloalkyl or 4–14C cycloalkyl radicals, each alkyl, cycloalkyl or cycloalkyl alkyl radical being optionally substituted by one or more halogen atoms selected from fluorine, chlorine and bromine atoms, provided that at least one of R$^1$ and R$^2$ is a halogen-substituted alkyl, cycloalkyl or cycloalkylalkyl radical and provided that there is no halogen substituent on the carbon atom of the alkyl, cycloalkyl or cycloalkylalkyl radical which is directly attached to the nitrogen atom;
ring X is selected from oxazole, thiazole, imidazole, 1,2,4-thiadiazole, 1,2,4-oxadiazole, 1,2,3-triazole, 1,2,4-triazole and pyrazole, and may, where possible, carry one or two optional substituents, the optional substituents on ring X being selected from fluorine, chlorine, bromine atoms and 1–6C alkyl, 1-6C alkoxy, 1-6C alkylthio, trifluoromethyl, hydroxy and amino radicals;

—A— is a phenylene or a 5-7C cycloalkylene radical or a 1-8C alkylene chain which is optionally substituted by one or two 1-3C alkyl radicals and into which is optionally inserted, as part of the backbone of the chain, one or two groups selected from oxygen and sulphur atoms and NH, 1-6C N-alkyl, cis or trans vinylene, ethynylene, phenylene and 5-7C cycloalkylene radicals, provided that the shortest link between ring X and $NR^4$ is of at least 3 atoms, provided that when the optional insertion is made in chain A which results in the inserted group being directly attached to $NR^4$ the inserted group is other than an oxygen or sulphur atom or an NH and N-alkyl radical, and provided that no two insertions selected from oxygen and sulphur atoms and NH and NH and N-alkyl radicals are directly attached one to the other;

D is an oxygen or sulphur atom;

$R^3$ is a 1-6C alkyl radical which is substituted by one, two or three halogen atoms or by one or two substituents selected from hydroxy, amino, cyano, nitro, carboxy, carbamoyl, 1-6C alkoxy, 1-6C alkylthio 1-6C alkylamino, 2-10C dialkylamino, 1-6C alkanoylamino, phenoxy, heteroaryl, heteroaryloxy, benzoylamino, 1-6C alkanoyl, benzoyl and 2-6C alkoxycarbonyl radicals;

or $R^3$ is a 2-6C alkenyl radical optionally substituted by one or two radicals selected from carboxy, carbamoyl, cyano, nitro, 2-6C alkoxycarbonyl, phenyl and heteroaryl radicals, or $R^3$ is a 2-6C alkynyl, phenyl, 7-11C phenylalkyl or heteroaryl radical or a radical of the formual $COR^7$ or $CONR^7R^8$ is which $R^7$ and $R^8$ are selected from hydrogen atoms and 1-6C alkyl and phenyl radicals, wherein when $R^3$ is or contains a heteroaryl radical that radical is furyl, thienyl, pyrazolyl tiazolyl, oxazolyl, imidazolyl, thiazolyl, oxadiazolyl, triazolyl, pynazolyl, pyridyl or pyrimidyl radical, or such a radical fused with a benzene ring;

and wherein $R^3$ is or contains an phenyl or heteroaryl radical, that radical may optionally by substituted by one or two substituents selected from halogen atoms and 1-6C alkyl, 1-6C alkoxy, 1-6C alkylthio, trifluoromethyl, hydroxy, amino, carbamoyl, 2-6C alkylcarbamoyl, 3-10C dialkylcarbamoyl, phenylcarbamoyl, diphenylcarbamoyl, sulphamoyl, 1-6C alkylsulphamoyl, 2-10C dialkylsulphamoyl, phenylsulphamoyl, diphenylsulphamoyl, 1-6C aminoalkyl, 2-10C alkylaminoalkyl, 3-15C dialkylaminoalkyl, 1-6C hydroxyalkyl and 2-10C alkoxyalkyl radicals and radicals of the formula III:

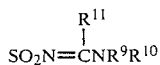

in which $R^9$ and $R^{10}$ are 1-6C alkyl radicals and $R^{11}$ is a hydrogen atom or $R^9$ is a 1-6C alkyl radical and $R^{10}$ and $R^{11}$ are joined to form, together with the nitrogen and carbon atoms to which they are attached, a pyrrolidine or piperidine ring, and, when the group inseted in A is an ethynylene radical, $R^3$ may also be a 1-6C alkyl radical;

$R^4$ is a hydrogen atom or a 1-6C alkyo radical; and the pharmaceutically-acceptable acid-addition salts thereof.

2. A guanidine derrivative of the formula I given in claim 1 in which $R^1$ and $R^2$ are selected from the group consisting of hydrogen, 2,2,2-trifluoroethyl, 2,2,2-trichloroethyl, 2-chloro-2,2-difluoroethyl, 2,2-dichloro-2-fluoroethyl, 2-bromo-2,2-difluoroethyl, 2,2-dibromo-2-fluoroethyl, 2-chloroethyl, 2,2-difluoroethyl, 2,2-dichloroethyl, 2-chloro-2-fluoroethyl, 2-bromo-2-fluoroethyl, 2,2,3,3-tetrafluoropropyl, 2,2,3,3,3-pentafluoropropyl, 1,1,1,3,3,3-hexafluoroisopropyl, 1,3-dichloro-1,1,3,3-tetrafluoroisopropyl, 1-chloro-1,1,3,3,3-pentafluoroisopropyl, 1,3-difluoroisopropyl, 2,2,3,3,4,4,4-heptafluorobutyl, 2,2,3,3-tetrafluorocyclopropyl, 2-chloro-2,3,3-trifluorocyclopropyl, 2-chloro-3,3-difluorocyclopropyl, 2,2,3,3,4,4-hexafluorocyclobutyl, 2-chloro-2,3,3,4,4-pentafluorocyclobutyl, (1,2,2,3,3-pentafluorocyclopropyl)methyl, (2-chloro-1,2,3,3-tetrafluorocyclopropyl)methyl, (1,2,2,3,3,4,4-heptafluorocyclobutyl)methyl, (2-chloro-1,2,3,3,4,4-hexafluorocyclobutyl)methyl, methyl, ethyl, propyl, isopropyl, butyl, cyclopropyl, cyclobutyl, cyclopropylmethyl and cyclopropylbutyl radicals provided that at least one of $R^1$ and $R^2$ is a halogen-substituted radical;

in ring X the optional substituents are selected from fluorine, chlorine and bromine atoms and methyl, methoxy, methylthio, trifluoromethyl, hydroxy and amino radials;

—A— is phenylene, cyclopentylene, cyclohexylene, trimethylene, tetramethylene, pentamethylene, thioethylene, thioterimethylene, thiotetramethylene, thiopentamethylene, oxyethylene, oxytrimethylene, oxytetramethylene, methylenethiomethylene, methylenethiothylene, methylenethiopropylene, methyleneoxymethylene, methyleneoxyethylene, ethyleneoxyethylene, oxy-2-methylethylene, thiopropylenethiomethylene, oxyethyleneoxymethylene, iminopropylene, iminoethylene, vinylenepropylene, oxymethylene-vinylene, 1,3-phenylene, 1,3-cycloptenylene, methylene-1,4-phenylene, ethyleneoxymethylene-1,4-phenylene, oxy-1,3-phenylenemethylene or thiomethyleneethynylenemethylene radical;

$R^3$ is a methyl, ethyl, propyl or isopropyl radical each substituted by one, two or three halogen atoms selected from fluorine, chlorine and bromine atoms or by one or two radicals selected from hydroxy, amino, cyano, nitro, carboxyl, carbamoyl, methoxy, methylthio, methylamino, dimethylamino, acetylamino, phenoxy, heteroaryl, heteroaryloxy, benzoylamino, acetyl, benzoyl and methoxycarbonyl radicals, or an allyl radical optionally substituted by one or two radicals selected from carboxy, carbamoyl, cyano, nitro, methoxycarbonyl, phenyl and heteroaryl radicals, or a propargyl, phenyl, benzyl or heteroaryl radical or radical of the formula $COR^7$ or $CONR^7R^8$ in which $R^7$ and $R^8$ are selected from hydrogen atoms and methyl and phenyl radicals;

wherein when $R^3$ is or contains a heteroaryl radical that radical is furyl, thienyl, pyrrolyl, tiazolyl, oxazolyl, imidazolyl, thiazolyl, oxadiazolyl, triazolyl, pyrazolyl, pyridyl or pyrimidyl radical or such a radical fused with a benzene ring;

and wherein $R^3$ is or contains a phenyl or heteroaryl radical, that radical may optionally be substituted by one or two substituents selected from fluorine, chlorine and bromine atoms and methyl, methoxy, methylthio, trifluoromethyl, hydroxy, amino, carbamoyl, methylcarbamoyl, dimethylcarbamoyl, phenycarbamoyl, diphenylcarbamoyl, sulphamoyl, methylsulphamoyl, dimethylsulphamoyl, phenylsulphamoyl, aminomethyl, methylaminomethyl, dimethylaminomethyl, hydroxymethyl and methoxymethyl radicals and radicals of the formula III given in claim 13 in which $R^9$ and $R^{10}$ are methyl radicals and $R^{11}$ is a hydrogen atom, or $R^9$ is a methyl radical and $R^{10}$ and $R^{11}$ are joined to form, together with the nitrogen and carbon atoms to which they are attached, a pyrrolidine or piperidine ring, and when the group inserted into A is an ethynylene radical, $R^3$ may also be a methyl radical;

and the pharmaceutically-acceptable acid-addition salts thereof.

3. A guanidine derivative as claimed in claim 2 in which $R^4$ is a hydrogen atom and D is an oxygen atom.

4. A guanidine derivative as claimed in claim 3 in which $R^2$ is a hydrogen atom and $R^1$ is 2,2,2-trifluoroethyl or 2,2,3,3-tetrafluoropropyl radical.

5. A guanidine derivative as claimed in claim 4 in which ring X is a 1,2,3-triazole ring.

6. A guanidine derivative as claimed in claim 5 in which ring X carries no optional substituent and A is a tetramethylene radical.

7. A guanidine derivative as claimed in claim 6 in which $R^3$ is a carbamoyl, methoxymethyl, thiazol-4-yl, furan-2-yl or pyrid-3-yl radical.

8. A guanidine derivative selected from the group consisting of N-(4-[4-(2-[2,2,2-trifluoroethyl]-guanidino)-1,2,3-triazol-2-yl]butyl)nicotinamide, N-(4-[4-(2-[2,2,2-trifluoroethyl]guanidino)-1,2,3-triazol-2-yl]butyl)oxamide and the pharmaceutically-acceptable acid-addition salts thereof.

9. A pharmaceutical composition which comprises a guanidine derivative as claimed in claim 1 in an amount effective to inhibit gastric acid secretion in a living animal and in association with a pharmaceutically-acceptable diluent or carrier.

10. A method of inhibiting gastric acid secretion in a living animal which comprising administering to the animal the composition of claim 9.

* * * * *